(12) United States Patent
Jeong et al.

(10) Patent No.: US 7,851,151 B2
(45) Date of Patent: Dec. 14, 2010

(54) HNF-1α GENE INCLUDING NOVEL SINGLE-NUCLEOTIDE POLYMORPHISM, PROTEIN ENCODED BY THE HNF-1α GENE, AND POLYNUCLEOTIDE, MICROARRAY, KIT, AND METHOD FOR DIAGNOSIS OF MODY3

(75) Inventors: Sung-young Jeong, Gyeonggi-do (KR); Jin-soon Hwang, Seoul (KR)

(73) Assignee: Samsung Electronics Co., Ltd. (KR)

( * ) Notice: Subject to any disclaimer, the term of this patent is extended or adjusted under 35 U.S.C. 154(b) by 768 days.

(21) Appl. No.: 11/049,806

(22) Filed: Feb. 3, 2005

(65) Prior Publication Data
US 2005/0181406 A1 Aug. 18, 2005

(30) Foreign Application Priority Data
Feb. 13, 2004 (KR) .................. 10-2004-0009626

(51) Int. Cl.
*C07H 21/04* (2006.01)
*C12Q 1/68* (2006.01)
*C12M 1/34* (2006.01)

(52) U.S. Cl. .............. 435/6; 435/287.2; 536/24.3; 536/23.1

(58) Field of Classification Search .............. None
See application file for complete search history.

(56) References Cited

U.S. PATENT DOCUMENTS

| 6,187,533 | B1 * | 2/2001 | Bell et al. .............. 435/6 |
| 2001/0053519 | A1 * | 12/2001 | Fodor et al. ............ 435/6 |
| 2002/0160360 | A1 * | 10/2002 | Chenchik et al. ......... 435/6 |
| 2003/0087798 | A1 * | 5/2003 | Raby et al. ............. 514/1 |
| 2003/0224355 | A1 * | 12/2003 | Bell et al. ............. 435/6 |

OTHER PUBLICATIONS

Yamagata, et al. Nature, 1996; 384:455-458.*
Hirschhorn et al. Genetics in Medicine. vol. 4, No. 2, pp. 45-61, Mar. 2002.*
Ioannidis. Nature Genetics, vol. 29, pp. 306-309, Nov. 2001.*
Hughes. Nature Medicine, 2007; 13:1008-1009.*
Manoj et al., Critical Reviews in Clinical Laboratory Sciences, 2004, 41: 1-39.*
GenBank Accession No. U72615, Mar. 8, 1997.*
GenBank Accession No. AA510037, Last updated Jul. 8, 1997.*
Tonooka, et al. Diabetologia, Dec. 2002; 45(12): 1709-1712.*
Ellard, Sian et al. Hepatocyte Nuclear Factor 1 Alpha Mutations in Maturity Onset Diabetes of the Young. 2000. Human Mutation. vol. 16 pp. 377-385.*
GenBank Accession NT_009775 GI 37544143 Entered Jan. 22, 2004.*
GenBank Accesion NM_000545 GI 38016908 Entered Dec. 23, 2003.*
Kaisaki, Pamela et al. Mutations in the Hepatocyte Nuclear Factor 1 alpha gene in MODY and early onset NIDDM. Diabetes 1997 vol. 46 pp. 528-535.*
Hwang et al.; "Genetic and Clinical Characteristics of Korean Maturity-Onset Diabetes of the Young (MODY) Patients"; Diabetes Research and Clinical Practice; vol. 74; pp. 75-81; 2006.
Velho et al.; "Maturity-Onset Diabetes of the Young (MODY): Genetic and Clinical Characteristics"; Hormone Research; vol. 57(suppl 1); pp. 29-33; 2002.

* cited by examiner

*Primary Examiner*—Stephen Kapushoc
*Assistant Examiner*—Amanda Shaw
(74) *Attorney, Agent, or Firm*—Cantor Colburn LLP

(57) ABSTRACT

Provided are a HNF-1 α gene including a novel single-nucleotide polymorphism and a protein encoded by the HNF-1 α gene, a polynucleotide associated with MODY3 diabetes based on the HNF-1 α gene, a microarray and a diagnostic kit including the polynucleotide, and a method for diagnosis of MODY3 diabetes.

6 Claims, 1 Drawing Sheet

US 7,851,151 B2

HNF-1α GENE INCLUDING NOVEL SINGLE-NUCLEOTIDE POLYMORPHISM, PROTEIN ENCODED BY THE HNF-1α GENE, AND POLYNUCLEOTIDE, MICROARRAY, KIT, AND METHOD FOR DIAGNOSIS OF MODY3

This application claims priority from Korean Patent Application No. 10-2004-0009626, filed on Feb. 13, 2004, in the Korean Intellectual Property Office, the disclosure of which is incorporated herein in its entirety by reference.

BACKGROUND OF THE INVENTION

1. Field of the Invention

The present invention relates to an HNF-1 α gene including a novel single-nucleotide polymorphism and a protein encoded by the HNF-1 α gene, a polynucleotide associated with MODY3 diabetes based on the HNF-1 α gene, a microarray and diagnostic kit including the polynucleotide, and a method for diagnosis of MODY3 diabetes.

2. Description of the Related Art

The genomes of all organisms undergo spontaneous mutation in the course of their continuing evolution, generating variant forms of progenitor nucleic acid sequences [Gusella, Ann. Rev. Biochem. 55, 831-854 (1986)]. The variant forms may confer an evolutionary advantage or disadvantage, relative to a progenitor form, or may be neutral. In some instances, a variant form confers a lethal disadvantage and is not transmitted to subsequent generations of the organism. In other instances, a variant form confers an evolutionary advantage to the species and is eventually incorporated into the DNA of most members of the species and effectively becomes the progenitor form. In many instances, both progenitor and variant form(s) survive and co-exist in a species population. The coexistence of multiple forms of a sequence gives rise to polymorphisms.

Several different types of polymorphisms have been known, including restriction fragment length polymorphisms (RFLPs), short tandem repeats (STRs), variable number tandem repeats (VNTRs), and single-nucleotide polymorphisms (SNPs). Among them, SNPs take the form of single-nucleotide variations between individuals of the same species. When SNPs occur in protein coding sequences, any one of the polymorphic forms may give rise to the expression of a defective or a variant protein. On the other hand, when SNPs occur in non-coding sequences, some of these polymorphisms may result in the expression of defective or variant proteins (e.g., as a result of defective splicing). Other SNPs have no phenotypic effects.

It is known that human SNPs occur at a frequency of 1 in about 1,000 bp. When such SNPs induce a phenotypic expression such as a disease, polynucleotides containing the SNPs can be used as primers or probes for diagnosis of a disease. Monoclonal antibodies specifically binding with the SNPs can also be used in diagnosis of a disease. Such SNPs can be detected by an analytic method such as polymerase chain reaction (PCR), sequencing, hybridization, and single-strand conformation polymorphism (SSCP).

It is known that 90-95% of total diabetes patients suffer type II diabetes mellitus. Type II diabetes mellitus is a disorder which is developed in persons who abnormally produce insulin or have low sensitivity to insulin, thereby resulting in large change in blood glucose level. When disorder of insulin secretion leads to the condition of type II diabetes mellitus, blood glucose cannot be transferred to body cells, which renders the conversion of food into energy difficult. It is known that a genetic cause has a role in type II diabetes mellitus. Other risk factors of type II diabetes mellitus are age over 45, familial history of diabetes mellitus, obesity, hypertension, and high cholesterol level. Currently, diagnosis of diabetes mellitus is mainly made by measuring a pathological phenotypic change, i.e., blood glucose level, using fasting blood glucose (FSB) test, oral glucose tolerance test (OGTT), and the like. When diagnosis of type II diabetes mellitus is made, type II diabetes mellitus can be prevented or its onset can be delayed by exercise, special diet, body weight control, drug therapy, and the like. In this regard, it can be said that type II diabetes mellitus is a disease in which early diagnosis is highly desirable.

MODY3 is a type of the maturity-onset diabetes of the young which is one of type II diabetes mellitus. It is estimated that MODY3 is responsible for 10-30% of type II diabetes mellitus. It is known that MODY3 is caused by disorder of HNF-1 α gene (also called as "MODY3 gene"). Millenium Pharmaceuticals Inc. reported that diagnosis and prognosis of type II diabetes mellitus can be made based on genotypic variations present on HNF1 gene [PR newswire, Sep. 1, 1998]. Even though there are reports about some genes associated with type II diabetes mellitus, researches into the incidence of type II diabetes mellitus have been focused on specific genes of some chromosomes in specific populations. For this reason, research results may vary according to human species. Furthermore, all causative genes responsible for MODY3 diabetes have not yet been identified. Diagnosis of MODY3 diabetes by such a molecular biological technique is now uncommon. In addition, early diagnosis before incidence of MODY3 diabetes is currently unavailable. Therefore, there is an increasing need to find new SNPs highly associated with MODY3 diabetes and related genes that are found in whole human genomes and to make early diagnosis of MODY3 diabetes using the SNPs and the related genes.

SUMMARY OF THE INVENTION

The present invention provides a polynucleotide useful for diagnosis or treatment of MODY3 diabetes.

The present invention also provides a microarray and kit useful for diagnosis of MODY3 diabetes.

The present invention also provides a method for efficient diagnosis of MODY3 diabetes.

The present invention also provides a variant HNF-1 α gene including a single-nucleotide polymorphism and a protein encoded by the variant HNF-1 α gene.

According to an aspect of the present invention, there is provided a polynucleotide for diagnosis or treatment of type II diabetes mellitus, including at least 10 contiguous nucleotides of a nucleotide sequence as set forth in SEQ ID NO: 3 and including a nucleotide at position 102 of the nucleotide sequence, or a complementary polynucleotide thereof.

According to another aspect of the present invention, there is provided a polynucleotide for diagnosis or treatment of type II diabetes mellitus, including at least 10 contiguous nucleotides of a nucleotide sequence as set forth in SEQ ID NO: 4 and including nucleotides at positions 102 and 103 of the nucleotide sequence, or a complementary polynucleotide thereof.

According to still another aspect of the present invention, there is provided a microarray for diagnosis of type II diabetes mellitus, including a substrate on which one of the polynucleotides of the present invention or the complementary polynucleotide thereof is immobilized.

According to still another aspect of the present invention, there is provided a kit for diagnosis of type II diabetes mellitus, including one of the polynucleotides of the present invention or the complementary polynucleotide thereof.

According to still another aspect of the present invention, there is provided a method for diagnosis of type II diabetes mellitus, which includes isolating a nucleic acid sample from an individual and determining a nucleotide sequence of a polymorphic site within a human HNF-1 α gene or a complementary polynucleotide thereof.

According to yet another aspect of the present invention, there is provided a variant HNF-1 α gene having a nucleotide sequence as set forth in SEQ ID NO: 1 and resulting from deletion of a cytidine nucleotide at position 1204 of a wild-type HNF-1 α gene (NCBI accession No. NM-000545).

According to a further aspect of the present invention, there is provided a variant HNF-1 α protein having an amino acid sequence as set forth in SEQ ID NO: 2.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
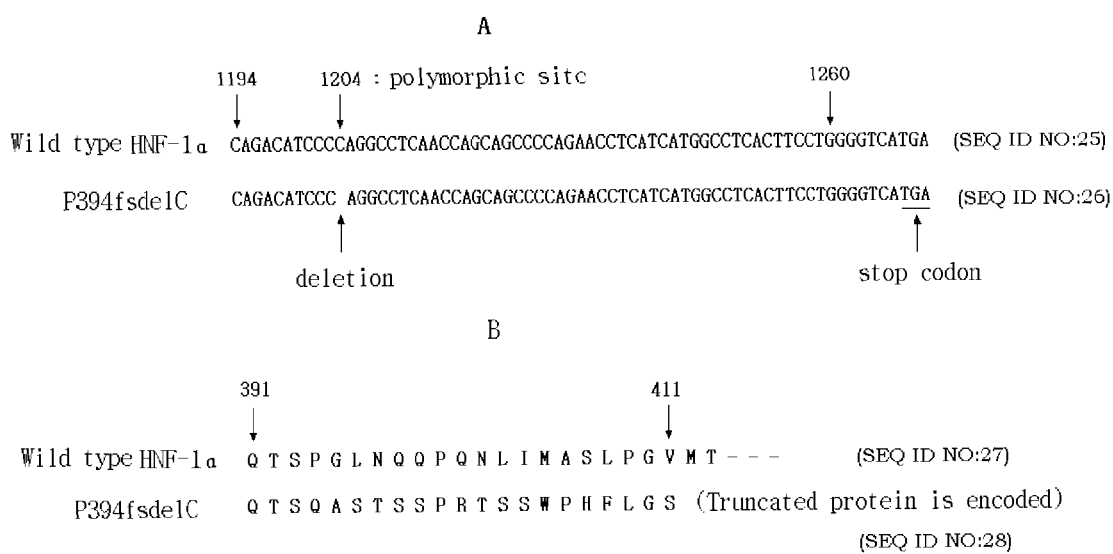
FIG. 1 is a view that illustrates the position of a polymorphic site of single-nucleotide polymorphism (SNP) P394fsdelC and a portion of a variant HNF-1 α protein encoded by the SNP.

The present inventors found a single-nucleotide polymorphism (SNP) specific to MODY3 patients. That is, the present inventors found a HNF-1 α gene variant that is found in MODY3 patients but not in normal persons.

Therefore, the present invention provides a polynucleotide for diagnosis or treatment of MODY3 diabetes, including at least 10 contiguous nucleotides of a nucleotide sequence as set forth in SEQ ID NO: 3 and including a nucleotide at position 102 of the nucleotide sequence, or a complementary polynucleotide thereof.

The nucleotide sequence of SEQ ID NO: 3 is a nucleotide sequence of exon 6 of a wild-type HNF-1 α gene. The present inventors found that a cytidine nucleotide at position 102 of the nucleotide sequence of SEQ ID NO: 3 is specifically absent in a MODY3 diabetes patient group. That is, wild-type and variant HNF-1 α genes are different in a nucleotide of the position 102 (called as "polymorphic site"). In this regard, a likelihood of being diagnosed as at risk of developing MODY3 diabetes can be determined by determining a nucleotide at position 102 of exon 6 of a wild-type HNF-1 α gene.

The present invention also provides a polynucleotide for diagnosis or treatment of MODY3 diabetes, including at least 10 contiguous nucleotides of a nucleotide sequence as set forth in SEQ ID NO: 4 and including nucleotides at positions 102 and 103 of the nucleotide sequence, or a complementary polynucleotide thereof.

The nucleotide sequence of SEQ ID NO: 4 is a nucleotide sequence of exon 6 of a variant HNF-1 α gene. The nucleotide sequence of SEQ ID NO: 4 results from deletion of the cytidine nucleotide of the position 102 of the nucleotide sequence of SEQ ID NO: 3 and is the same as that of SEQ ID NO: 3 except the cytidine deletion. The nucleotide sequence of SEQ ID NO: 4 is specifically found in a MODY3 diabetes patient group. Therefore, the polynucleotide including the nucleotides of the positions 102 and 103 of SEQ ID NO: 4 and the complementary polynucleotide thereof cannot be completely hybridized with the nucleotide sequence of SEQ ID NO: 3 which is a wild-type sequence. In this respect, a likelihood of being diagnosed as at risk of developing MODY3 diabetes can be determined by determining the nucleotides of the positions 102 and 103 of SEQ ID NO: 4 or the nucleotide of the position 102 of SEQ ID NO: 3. The polynucleotide for diagnosis or treatment of MODY3 diabetes including both the nucleotides of the positions 102 and 103 of SEQ ID NO: 4 according to the present invention or the complementary polynucleotide thereof can be efficiently used in determining the nucleotides of the positions 102 and 103 of SEQ ID NO: 4 or the nucleotide of the position 102 of SEQ ID NO: 3 of an individual.

The polynucleotides of the present invention are used for specifically determining the SNP site newly found by the present inventors and each has a polymorphic site. In this regard, the polynucleotides of the present invention can be efficiently used in a method and an apparatus for diagnosis or treatment of MODY3 diabetes for a nucleic acid sample obtained from an individual. For example, in a case where the polynucleotides of the present invention are used as primers for PCR, each of the polynucleotides of the present invention can amplify one of a wild-type nucleotide sequence and a variant nucleotide sequence since it includes a wild-type or variant nucleotide in the polymorphic site. Whether a genomic DNA or mRNA of an individual is a wild-type or a variant can be determined by comparing primers used and PCR products. Therefore, it can be determined whether the individual has a higher likelihood of being diagnosed as at risk of developing MODY3 diabetes. In an exemplary embodiment of the present invention, the polynucleotides of the present invention are used as allele-specific primers. The polynucleotides of the present invention can also be used as allele-specific probes in an analytic method such as southern blot, as previously described in terms of the primers for PCR.

Therefore, in an exemplary embodiment of the present invention, the polynucleotides of the present invention are primer or probe polynucleotides. Preferably, the polynucleotides of the present invention have 10 or more nucleotides. The polynucleotides of the present invention are 10 to 400 nucleotides in length, preferably 10 to 100 nucleotides in length, and more preferably 10 to 50 nucleotides in length.

In the present invention, the term "primer" refers to a single stranded oligonucleotide that acts as a starting point of template-directed DNA synthesis under appropriate conditions, for example in a buffer containing four different nucleoside triphosphates and polymerase such as DNA or RNA polymerase or reverse transcriptase, and at an appropriate temperature. The appropriate length of the primer may vary according to the purpose of use, generally 15 to 30 nucleotides. Generally, a shorter primer molecule requires a lower temperature to form a stable hybrid with a template. A primer sequence is not necessarily completely complementary with a template but must be complementary enough to hybridize with the template. Preferably, the 3' end of the primer is aligned with the polymorphic site of SEQ ID NO: 3 or 4, i.e., the nucleotide at the position 102 of SEQ ID NO: 3 or the nucleotides at the positions 102 and 103 of SEQ ID NO: 4. The primer is hybridized with a target DNA containing a polymorphic site and starts an allelic amplification in which the primer exhibits complete homology with the target DNA. The primer is used in pair with a second primer hybridizing with an opposite strand. Amplified products are obtained by amplification using the two primers, which means that there is a specific allelic form. The primer of the present invention includes a polynucleotide fragment used in a ligase chain reaction (LCR).

In the present invention, the term "probe" refers to a hybridization probe, that is, an oligonucleotide capable of sequence-specifically binding with a complementary strand of a nucleic acid. Such a probe includes a peptide nucleic acid as disclosed in Science 254, 1497-1500 (1991) by Nielsen et al. The probe according to the present invention is an allele-specific probe. In this regard, when there are polymorphic sites in nucleic acid fragments derived from two members of the same species, the probe is hybridized with DNA fragments derived from one member but is not hybridized with DNA fragments derived from the other member. In this case, hybridization conditions should be stringent enough to allow hybridization with only one allele by significant difference in hybridization strength between alleles. Preferably, the central portion of the probe of the present invention, that is, position 7 for a 15 nucleotide probe, or position 8 or 9 for a 16 nucleotide probe, is aligned with the polymorphic site of SEQ ID NO: 3 or 4. Therefore, there can be caused a significant difference in hybridization between alleles. The probe of the present invention can be used in diagnostic methods for detecting alleles. The diagnostic methods include nucleic acid hybridization-based detection methods, e.g., southern blot. In a case where DNA chips are used for the nucleic acid hybridization-based detection methods, the probe may be provided as an immobilized form on a substrate of a DNA chip.

The present invention also provides a microarray for diagnosis of MODY3 diabetes, including a substrate on which one of the polynucleotides of the present invention or the complementary polynucleotide thereof is immobilized.

As used herein, the term "polynucleotide microarray" indicates an analysis system in which polynucleotide groups are immobilized in a high density on a substrate, in detail, a microarray in which each of the polynucleotide groups is immobilized on a predetermined region. Such a microarray is well known in the pertinent art. Examples of the microarray are disclosed in U.S. Pat. Nos. 5,445,934 and 5,744,305. A fabrication method for the polynucleotide microarray is illustrated in U.S. Pat. Nos. 5,744,305, 5,143,854, and 5,424,186. The above patent documents about polynucleotide microarrays and fabrication methods thereof are incorporated herein in their entireties by reference.

The present invention also provides a kit for diagnosis of MODY3 diabetes, including one of the polynucleotides of the present invention or the complementary polynucleotide thereof. The kit may include reagents necessary for polymerization, for example dNTPs, various polymerases, and a colorant, in addition to the polynucleotides of the present invention.

The present invention also provides a method for diagnosis of MODY3 diabetes, which includes isolating a nucleic acid sample from an individual and determining a nucleotide sequence of a polymorphic site within a human HNF-1 α gene or a complementary polynucleotide thereof.

The operation of isolating the nucleic acid sample from an individual is well known in the pertinent art. For example, the nucleic acid sample can be obtained by amplifying a target nucleic acid by PCR followed by purification. In addition to PCR, there may be used LCR (Wu and Wallace, *Genomics* 4, 560 (1989), Landegren et al., *Science* 241, 1077 (1988)), transcription amplification (Kwoh et al., *Proc. Natl. Acad. Sci. USA* 86, 1173 (1989)), self-sustained sequence replication (Guatelli et al., *Proc. Natl. Acad. Sci. USA* 87, 1874 (1990)), or nucleic acid sequence based amplification (NASBA). The last two methods are related with isothermal reaction based on isothermal transcription and produce 30 or 100-fold RNA single strands and DNA double strands as amplification products.

The nucleic acid sample can also be obtained from human tissue or blood stream. The nucleic acid sample may not necessarily be a pure nucleic acid and may vary according to an analytic method. For example, in PCR or in situ hybridization, a tissue or blood stream itself may be used as the nucleic acid sample without the separation of a nucleic acid from the tissue or the blood stream. The nucleic acid sample may be a natural nucleic acid, including genomic DNA or RNA (including mRNA).

As used herein, the term "human HNF-1 α gene" is used as the meaning including both wild-type and variant HNF-1 α genes. That is, the presence of a SNP can be determined by determining a nucleotide of position 1204 which is a polymorphic site of a wild-type HNF-1 α gene (NCBI accession No. NM-000545) or determining nucleotides of positions 1203 and 1204 which is a polymorphic site of SEQ ID NO: 4, followed by comparison with the nucleotide sequence of the wild-type gene.

In the present invention, the determination of the nucleotide sequence of the polymorphic site of the human HNF-1 α gene can be carried out by using a method known in the pertinent art. Such a method may include sequencing, PCR, RT-PCR, and a hybridization-based method such as southern blot or northern blot, but is not limited thereto. In such a sequence determination, the polynucleotides of the present invention or the complementary polynucleotides thereof can be efficiently used as synthetic primers, PCR primers, or probes.

In the method of the present invention, whether an individual has a higher likelihood of being diagnosed as at risk of developing MODY3 can be determined, for example, by determining the nucleotide sequence of the human HNF-1 α gene of the nucleic acid sample isolated according to the above description or its fragment including the polymorphic site, followed by comparison with the nucleotide sequence of the polymorphic site of the wild-type human HNF-1 α gene. Preferably, when the HNF-1 α gene of the nucleic acid sample isolated from the individual includes a cytidine (C) deletion, relative to the polymorphic site of the wild type HNF-1 α gene, it is determined that the individual has a higher likelihood of being diagnosed as at risk of developing MODY3.

The present invention also provides a variant HNF-1 α gene having a nucleotide sequence as set forth in SEQ ID NO: 1 and resulting from deletion of a cytidine nucleotide at position 1204 of a wild-type HNF-1 α gene (NCBI accession No. NM-000545).

The present invention also provides a variant HNF-1 α protein having an amino acid sequence as set forth in SEQ ID NO: 2.

Hereinafter, the present invention will be described more specifically by Example. However, the following Example is provided only for illustration and thus the present invention is not limited thereto.

Example

In this Example, genomic DNAs were extracted from blood streams of a clinical MODY putative patient group, followed by amplification of HNF-1 α genes, sequencing, and comparison with the sequence of a wild-type gene. As a result, a SNP specific to the patient group was detected.

1. Amplification of 10 Exons of MODY3 Gene

Genomic DNAs were extracted from blood streams of MODY3 diabetes patients and normal persons. DNA extraction was performed according to a known extraction method (Molecular cloning: A Laboratory Manual, p 392, Sambrook, Fritsch and Maniatis, 2nd edition, Cold Spring Harbor Press, 1989) and the specification of a commercial kit (QIAGEN Blood Midi kit). Among extracted DNAs, only DNAs having a purity ($A_{260}/A_{280}$ nm) of at least 1.7 were used.

The 10 exons of the HNF-1 α gene was amplified by PCR using the extracted DNAs as templates and primers capable of amplifying the 10 exons of the HNF-1 α gene. In detail, the PCR was performed by a common PCR method using 1-100 μg of each of the genomic DNAs as a template, Taq polymerase, and primers presented in Table 1 below. The thermal cycles of the PCR were as follows: incubation at 95° C. for 5 minutes; 30 cycles at 95° C. for 30 seconds, at 64° C. for 15 seconds, and at 72° C. for 1 minute; incubation at 72° C. for 3 minutes and storage at 4° C. PCR products were used in sequencing after being purified by QIAquick kit.

TABLE 1

PCR primers used in amplification of MODY3 gene

| Name | Sequence |
|---|---|
| Mody 3 promoter sense(T7) | SEQ ID NO: 5 |
| Mody 3 promoter antisense(T3) | SEQ ID NO: 6 |
| Mody 3 exon1 sense(T7) | SEQ ID NO: 7 |
| Mody 3 exon1 antisense(T3) | SEQ ID NO: 8 |
| Mody 3 exon2 sense(T7) | SEQ ID NO: 9 |
| Mody 3 exon2 antisense(T3) | SEQ ID NO: 10 |
| Mody 3 exon3 sense(T7) | SEQ ID NO: 11 |
| Mody 3 exon3 antisense(T3) | SEQ ID NO: 12 |
| Mody 3 exon4 sense(T7) | SEQ ID NO: 13 |
| Mody 3 exon4 antisense(T3) | SEQ ID NO: 14 |
| Mody 3 exon5 sense(T7) | SEQ ID NO: 15 |
| Mody 3 exon5 antisense(T3) | SEQ ID NO: 16 |
| Mody 3 exon6 sense(T7) | SEQ ID NO: 17 |
| Mody 3 exon6 antisense(T3) | SEQ ID NO: 18 |
| Mody 3 exon7 sense(T7) | SEQ ID NO: 19 |
| Mody 3 exon7 antisense(T3) | SEQ ID NO: 20 |
| Mody 3 exon8 & 9 sense(T7) | SEQ ID NO: 21 |
| Mody 3 exon8 & 9 antisense(T3) | SEQ ID NO: 22 |

TABLE 1-continued

PCR primers used in amplification of MODY3 gene

| Name | Sequence |
|---|---|
| Mody 3 exon10 sense(T7) | SEQ ID NO: 23 |
| Mody 3 exon10 antisense(T3) | SEQ ID NO: 24 |

2. Analysis of SNPs in Amplified Target DNAs

The 10 exons of the amplified HNF-1 α gene were sequenced. The sequencing was performed as follows: sequencing PCR was performed using primers for each exon according to the ABI BigDye terminator cycle sequencing ready reaction kit method. PCR products were precipitated by alcohol, suspended in formaldehyde, heated at 95° C. for 5 minutes, and directly placed on 4° C. ice. The sequencing of the 10 exons of the HNF-1 α gene thus obtained was performed in ABI PRISM 3700 Genetic Analyzer. The sequence analysis was performed using DNAstar program.

According to the analysis results, the MODY3 patient group carried a deletion of the cytidine nucleotide at position 1204 of the wild-type HNF-1 α gene (NCBI accession No. NM-000545). Such a deletion was observed at a frequency of 1 in 300 patients but was not observed in the normal persons. Such a SNP was designated as "P394fsdelC". The SNP resulted in an upstream shift of a translation stop codon, relative to the wild-type HNF-1 α gene. These analysis results are shown in FIG. 1. FIG. 1 illustrates the position of a polymorphic site of the SNP, P394fsdelC, and a variant HNF-1 α protein encoded by the SNP.

A polynucleotides of the present invention can be used in diagnosis, treatment, and fingerprinting analysis of MODY3 diabetes.

A microarray and kit including the polynucleotide of the present invention can be used for efficient diagnosis of MODY3 diabetes.

A method for diagnosis of MODY3 diabetes of the present invention can efficiently detect the presence or a risk of MODY3 diabetes.

A variant HNF-1 α gene or variant protein of the present invention can be efficiently used in development of drugs for diagnosis or treatment of MODY3 diabetes.

What is claimed is:

1. An isolated polynucleotide comprising at least 30 contiguous nucleotides of SEQ ID NO: 4, wherein the at least 30 contiguous nucleotides include the nucleotides at positions 102 and 103 of SEQ ID NO: 4, or the complement thereof.

2. An isolated variant HNF-1α gene consisting of SEQ ID NO: 1.

3. The isolated polynucleotide of claim 1, which is 30 to 100 nucleotides in length, or the complement thereof.

4. The isolated polynucleotide of claim 1, which is a primer or a probe.

5. A microarray comprising a substrate on which the isolated polynucleotide of claim 1 or the complement thereof is immobilized.

6. A kit comprising the isolated polynucleotide of claim 1 or the complement thereof.

* * * * *

SEQUENCE LISTING

```
<160> NUMBER OF SEQ ID NOS: 28

<210> SEQ ID NO 1
<211> LENGTH: 1259
<212> TYPE: DNA
<213> ORGANISM: Homo sapiens
<220> FEATURE:
<221> NAME/KEY: CDS
<222> LOCATION: (24)..(1256)

<400> SEQUENCE: 1
cgtggccctg tggcagccga gcc atg gtt tct aaa ctg agc cag ctg          47
                        Met Val Ser Lys Leu Ser Gln Leu
                         1               5 cag acg gag ctc ctg gcg gcc ctg ctc gag tca ggg ctg agc aaa gag   95
Gln Thr Glu Leu Leu Ala Ala Leu Leu Glu Ser Gly Leu Ser Lys Glu
     10              15                  20 gca ctg atc cag gca ctg ggt gag ccg ggg ccc tac ctc ctg gct gga  143
```

-continued

```
                Ala Leu Ile Gln Ala Leu Gly Glu Pro Gly Pro Tyr Leu Leu Ala Gly
                 25                  30                  35                  40 gaa ggc ccc ctg gac aag ggg gag tcc tgc ggc ggt cga ggg gag                   191
Glu Gly Pro Leu Asp Lys Gly Glu Ser Cys Gly Gly Arg Gly Glu
                     45                  50                  55 ctg gct gag ctg ccc aat ggg ctg ggg gag act cgg ggc tcc gag gac               239
Leu Ala Glu Leu Pro Asn Gly Leu Gly Glu Thr Arg Gly Ser Glu Asp
             60                  65                  70 gag acg gac gac gat ggg gaa gac ttc acg cca ccc atc ctc aaa gag               287
Glu Thr Asp Asp Asp Gly Glu Asp Phe Thr Pro Pro Ile Leu Lys Glu
                 75                  80                  85 ctg gag aac ctc agc cct gag gag gcg gcc cac cag aaa gcc gtg gtg               335
Leu Glu Asn Leu Ser Pro Glu Glu Ala Ala His Gln Lys Ala Val Val
             90                  95                 100 gag acc ctt ctg cag gag gac ccg tgg cgt gtg gcg aag atg gtc aag               383
Glu Thr Leu Leu Gln Glu Asp Pro Trp Arg Val Ala Lys Met Val Lys
105                 110                 115                 120 tcc tac ctg cag cag cac aac atc cca cag cgg gag gtg gtc gat acc               431
Ser Tyr Leu Gln Gln His Asn Ile Pro Gln Arg Glu Val Val Asp Thr
                125                 130                 135 act ggc ctc aac cag tcc cac ctg tcc caa cac ctc aac aag ggc act               479
Thr Gly Leu Asn Gln Ser His Leu Ser Gln His Leu Asn Lys Gly Thr
            140                 145                 150 ccc atg aag acg cag aag cgg gcc gcc ctg tac acc tgg tac gtc cgc               527
Pro Met Lys Thr Gln Lys Arg Ala Ala Leu Tyr Thr Trp Tyr Val Arg
                155                 160                 165 aag cag cga gag gtg gcg cag cag ttc acc cat gca ggg cag gga ggg               575
Lys Gln Arg Glu Val Ala Gln Gln Phe Thr His Ala Gly Gln Gly Gly
170                 175                 180 ctg att gaa gag ccc aca ggt gat gag cta cca acc aag aag ggg cgg               623
Leu Ile Glu Glu Pro Thr Gly Asp Glu Leu Pro Thr Lys Lys Gly Arg
185                 190                 195                 200 agg aac cgt ttc aag tgg ggc cca gca tcc cag cag atc ctg ttc cag               671
Arg Asn Arg Phe Lys Trp Gly Pro Ala Ser Gln Gln Ile Leu Phe Gln
                205                 210                 215 gcc tat gag agg cag aag aac cct agc aag gag gag cga gag acg cta               719
Ala Tyr Glu Arg Gln Lys Asn Pro Ser Lys Glu Glu Arg Glu Thr Leu
            220                 225                 230 gtg gag gag tgc aat agg gcg gaa tgc atc cag aga ggg gtg tcc cca               767
Val Glu Glu Cys Asn Arg Ala Glu Cys Ile Gln Arg Gly Val Ser Pro
                235                 240                 245 tca cag gca cag ggg ctg ggc tcc aac ctc gtc acg gag gtg cgt gtc               815
Ser Gln Ala Gln Gly Leu Gly Ser Asn Leu Val Thr Glu Val Arg Val
            250                 255                 260 tac aac tgg ttt gcc aac cgg cgc aaa gaa gaa gcc ttc cgg cac aag               863
Tyr Asn Trp Phe Ala Asn Arg Arg Lys Glu Glu Ala Phe Arg His Lys
265                 270                 275                 280 ctg gcc atg gac acg tac agc ggg ccc ccc ggg cca ggc ccg gga               911
Leu Ala Met Asp Thr Tyr Ser Gly Pro Pro Gly Pro Gly Pro Gly
                285                 290                 295 cct gcg ctg ccc gct cac agc tcc cct ggc ctg cct cca cct gcc ctc               959
Pro Ala Leu Pro Ala His Ser Ser Pro Gly Leu Pro Pro Pro Ala Leu
            300                 305                 310 tcc ccc agt aag gtc cac ggt gtg cgc tat gga cag cct gcg acc agt              1007
Ser Pro Ser Lys Val His Gly Val Arg Tyr Gly Gln Pro Ala Thr Ser
                315                 320                 325 gag act gca gaa gta ccc tca agc agc ggc ggt ccc tta gtg aca gtg              1055
Glu Thr Ala Glu Val Pro Ser Ser Ser Gly Gly Pro Leu Val Thr Val
            330                 335                 340
```

-continued

```
tct aca ccc ctc cac caa gtg tcc ccc acg ggc ctg gag ccc agc cac      1103
Ser Thr Pro Leu His Gln Val Ser Pro Thr Gly Leu Glu Pro Ser His
345                 350                 355                 360 agc ctg ctg agt aca gaa gcc aag ctg gtc tca gca gct ggg ggc ccc      1151
Ser Leu Leu Ser Thr Glu Ala Lys Leu Val Ser Ala Ala Gly Gly Pro
                365                 370                 375 ctc ccc cct gtc agc acc ctg aca gca ctg cac agc ttg gag cag aca      1199
Leu Pro Pro Val Ser Thr Leu Thr Ala Leu His Ser Leu Glu Gln Thr
            380                 385                 390 tcc cag gcc tca acc agc agc ccc aga acc tca tca tgg cct cac ttc      1247
Ser Gln Ala Ser Thr Ser Ser Pro Arg Thr Ser Ser Trp Pro His Phe
        395                 400                 405 ctg ggg tca tga                                                      1259
Leu Gly Ser
    410

<210> SEQ ID NO 2
<211> LENGTH: 411
<212> TYPE: PRT
<213> ORGANISM: Homo sapiens

<400> SEQUENCE: 2

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270
```

```
Lys Glu Glu Ala Phe Arg His Lys Leu Ala Met Asp Thr Tyr Ser Gly
            275                 280                 285

Pro Pro Pro Gly Pro Gly Pro Ala Leu Pro Ala His Ser Ser
        290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
            355                 360                 365

Leu Val Ser Ala Ala Gly Gly Pro Leu Pro Pro Val Ser Thr Leu Thr
            370                 375                 380

Ala Leu His Ser Leu Glu Gln Thr Ser Gln Ala Ser Thr Ser Ser Pro
385                 390                 395                 400

Arg Thr Ser Ser Trp Pro His Phe Leu Gly Ser
                405                 410
```

<210> SEQ ID NO 3
<211> LENGTH: 247
<212> TYPE: DNA
<213> ORGANISM: Homo sapiens

<400> SEQUENCE: 3

```
cccggacaca gcttggcttc ccctcgtagg tctcagcagc tgggggcccc ctccccctg     60
tcagcaccct gacagcactg cacagcttgg agcagacatc cccaggcctc aaccagcagc  120
cccagaacct catcatggcc tcacttcctg gggtcatgac catcgggcct ggtgagcctg  180
cctccctggg tcctacgttc accaacacag gtgcctccac cctggtcatc ggtaagctgg  240
tggggat                                                            247
```

<210> SEQ ID NO 4
<211> LENGTH: 246
<212> TYPE: DNA
<213> ORGANISM: Homo sapiens

<400> SEQUENCE: 4

```
cccggacaca gcttggcttc ccctcgtagg tctcagcagc tgggggcccc ctccccctg     60
tcagcaccct gacagcactg cacagcttgg agcagacatc ccaggcctca accagcagcc  120
ccagaacctc atcatggcct cacttcctgg ggtcatgacc atcgggcctg gtgagcctgc  180
ctccctgggt cctacgttca ccaacacagg tgcctccacc ctggtcatcg gtaagctggt  240
ggggat                                                              246
```

<210> SEQ ID NO 5
<211> LENGTH: 41
<212> TYPE: DNA
<213> ORGANISM: Artificial Sequence
<220> FEATURE:
<223> OTHER INFORMATION: sense primer for amplifying promoter of MODY3
      gene

<400> SEQUENCE: 5

```
taatacgact cactataggg tggccgtgag catcctctgc c                        41
```

<210> SEQ ID NO 6
<211> LENGTH: 39

```
<212> TYPE: DNA
<213> ORGANISM: Artificial Sequence
<220> FEATURE:
<223> OTHER INFORMATION: antisense primer for amplifying promoter of
      MODY3 gene

<400> SEQUENCE: 6
gtaaccctca ctaaagggac gtgggttgcg tttgcctgc                              39

<210> SEQ ID NO 7
<211> LENGTH: 40
<212> TYPE: DNA
<213> ORGANISM: Artificial Sequence
<220> FEATURE:
<223> OTHER INFORMATION: sense primer for amplifying exon 1 of MODY3
      gene

<400> SEQUENCE: 7
taatacgact cactataggg cgtggccctg tggcagccga                             40

<210> SEQ ID NO 8
<211> LENGTH: 40
<212> TYPE: DNA
<213> ORGANISM: Artificial Sequence
<220> FEATURE:
<223> OTHER INFORMATION: antisense primer for amplifying exon 1 of
      MODY3 gene

<400> SEQUENCE: 8
gtaaccctca ctaaagggag ggctcgttag gagctgaggg                             40

<210> SEQ ID NO 9
<211> LENGTH: 42
<212> TYPE: DNA
<213> ORGANISM: Artificial Sequence
<220> FEATURE:
<223> OTHER INFORMATION: sense primer for amplifying exon 2 of MODY3
      gene

<400> SEQUENCE: 9
taatacgact cactataggg cccttgctga gcagatcccg tc                          42

<210> SEQ ID NO 10
<211> LENGTH: 40
<212> TYPE: DNA
<213> ORGANISM: Artificial Sequence
<220> FEATURE:
<223> OTHER INFORMATION: antisense primer for amplifying exon 2 of
      MODY3 gene

<400> SEQUENCE: 10
gtaaccctca ctaaagggag ggatggtgaa gcttccagcc                             40

<210> SEQ ID NO 11
<211> LENGTH: 40
<212> TYPE: DNA
<213> ORGANISM: Artificial Sequence
<220> FEATURE:
<223> OTHER INFORMATION: sense primer for amplifying exon 3 of MODY3
      gene

<400> SEQUENCE: 11
taatacgact cactataggg gcaaggtcag gggaatggac                             40

<210> SEQ ID NO 12
<211> LENGTH: 42
<212> TYPE: DNA
```

```
<213> ORGANISM: Artificial Sequence
<220> FEATURE:
<223> OTHER INFORMATION: antisense primer for amplifying exon 3 of
      MODY3 gene

<400> SEQUENCE: 12
gtaaccctca ctaaagggac gccgttgtac ctattgcact cc                         42

<210> SEQ ID NO 13
<211> LENGTH: 43
<212> TYPE: DNA
<213> ORGANISM: Artificial Sequence
<220> FEATURE:
<223> OTHER INFORMATION: sense primer for amplifying exon 4 of
      MODY3 gene

<400> SEQUENCE: 13
taatacgact cactataggg ggctcatggg tggctatttc tgc                        43

<210> SEQ ID NO 14
<211> LENGTH: 42
<212> TYPE: DNA
<213> ORGANISM: Artificial Sequence
<220> FEATURE:
<223> OTHER INFORMATION: antisense primer for amplifying exon 4 of
      MODY3 gene

<400> SEQUENCE: 14
gtaaccctca ctaaagggac gtgtcccttg tccccacata cc                         42

<210> SEQ ID NO 15
<211> LENGTH: 42
<212> TYPE: DNA
<213> ORGANISM: Artificial Sequence
<220> FEATURE:
<223> OTHER INFORMATION: sense primer for amplifying exon 5 of
      MODY3 gene

<400> SEQUENCE: 15
taatacgact cactataggg tgctgaggca ggacactgct tc                         42

<210> SEQ ID NO 16
<211> LENGTH: 42
<212> TYPE: DNA
<213> ORGANISM: Artificial Sequence
<220> FEATURE:
<223> OTHER INFORMATION: antisense primer for amplifying exon 5 of
      MODY3 gene

<400> SEQUENCE: 16
gtaaccctca ctaaagggat acaagcaagg acactcacca gc                         42

<210> SEQ ID NO 17
<211> LENGTH: 41
<212> TYPE: DNA
<213> ORGANISM: Artificial Sequence
<220> FEATURE:
<223> OTHER INFORMATION: sense primer for amplifying exon 6 of MODY3
      gene

<400> SEQUENCE: 17
taatacgact cactataggg cccggacaca gcttggcttc c                          41

<210> SEQ ID NO 18
<211> LENGTH: 42
<212> TYPE: DNA
<213> ORGANISM: Artificial Sequence
```

```
<220> FEATURE:
<223> OTHER INFORMATION: antisense primer for amplifying exon 6 of
      MODY3 gene

<400> SEQUENCE: 18
gtaaccctca ctaaagggaa tccccaccag cttaccgatg ac                          42

<210> SEQ ID NO 19
<211> LENGTH: 40
<212> TYPE: DNA
<213> ORGANISM: Artificial Sequence
<220> FEATURE:
<223> OTHER INFORMATION: sense primer for amplifying exon 7 of
      MODY3 gene

<400> SEQUENCE: 19
taatacgact cactataggg caggcctggc ctccacgcag                             40

<210> SEQ ID NO 20
<211> LENGTH: 40
<212> TYPE: DNA
<213> ORGANISM: Artificial Sequence
<220> FEATURE:
<223> OTHER INFORMATION: antisense primer for amplifying exon 7 of
      MODY3 gene

<400> SEQUENCE: 20
gtaaccctca ctaaagggag gggctctgca gctgagccat                             40

<210> SEQ ID NO 21
<211> LENGTH: 41
<212> TYPE: DNA
<213> ORGANISM: Artificial Sequence
<220> FEATURE:
<223> OTHER INFORMATION: sense primer for amplifying exon 8 and 9 of
      MODY3 gene

<400> SEQUENCE: 21
taatacgact cactataggg ggcccagtac acccacacgg g                           41

<210> SEQ ID NO 22
<211> LENGTH: 40
<212> TYPE: DNA
<213> ORGANISM: Artificial Sequence
<220> FEATURE:
<223> OTHER INFORMATION: antisense primer for amplifying exon 8 and 9
      of MODY3 gene

<400> SEQUENCE: 22
gtaaccctca ctaaagggag ggcagggaca gtaagggagg                             40

<210> SEQ ID NO 23
<211> LENGTH: 41
<212> TYPE: DNA
<213> ORGANISM: Artificial Sequence
<220> FEATURE:
<223> OTHER INFORMATION: sense primer for amplifying exon 10 of MODY3
      gene

<400> SEQUENCE: 23
taatacgact cactataggg gccttgtttg cctctgcagt g                           41

<210> SEQ ID NO 24
<211> LENGTH: 41
<212> TYPE: DNA
<213> ORGANISM: Artificial Sequence
<220> FEATURE:
```

```
<223> OTHER INFORMATION: antisense primer for amplifying exon 10 of
      MODY3 gene

<400> SEQUENCE: 24
gtaaccctca ctaaagggag gccatctggg tggagatgaa g                         41

<210> SEQ ID NO 25
<211> LENGTH: 67
<212> TYPE: DNA
<213> ORGANISM: Homo sapiens
<220> FEATURE:
<221> NAME/KEY: misc_feature
<222> LOCATION: (1)..(67)
<223> OTHER INFORMATION: wild type HNF-1a

<400> SEQUENCE: 25
cagacatccc caggcctcaa ccagcagccc cagaacctca tcatggcctc acttcctggg     60
gtcatga                                                               67

<210> SEQ ID NO 26
<211> LENGTH: 66
<212> TYPE: DNA
<213> ORGANISM: Homo sapiens
<220> FEATURE:
<221> NAME/KEY: misc_feature
<222> LOCATION: (1)..(66)
<223> OTHER INFORMATION: P394fsdelC of HNF-1a

<400> SEQUENCE: 26
cagacatccc aggcctcaac cagcagcccc agaacctcat catggcctca cttcctgggg     60
tcatga                                                                66

<210> SEQ ID NO 27
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: wild type HNF-1a

<400> SEQUENCE: 27

Gln Thr Ser Pro Gly Leu Asn Gln Gln Pro Gln Asn Leu Ile Met Ala
 1               5                  10                  15

Ser Leu Pro Gly Val Met Thr
            20

<210> SEQ ID NO 28
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: truncated HNF-1a: P394fsdelC

<400> SEQUENCE: 28

Gln Thr Ser Gln Ala Ser Thr Ser Ser Pro Arg Thr Ser Ser Trp Pro
 1               5                  10                  15

His Phe Leu Gly Ser
            20
```